(12) United States Patent
Vicente Miralles (10) Patent No.: US 11,975,201 B2
(45) Date of Patent: May 7, 2024

(54) FASTENING SYSTEM FOR AN ELECTRICAL STIMULATION GENERATOR

(71) Applicants: Raimundo Vicente Miralles, Elche (ES); FUNDACIÓN UNIVERSITAS MIGUEL HERNÁNDEZ DE LA COMUNITAT VALENCIANA, Elche (ES)

(72) Inventor: Raimundo Vicente Miralles, Elche (ES)

(73) Assignees: Raimundo Vicente Miralles, Elche (ES); FUNDACIÓN UNIVERSITAS MIGUEL HERNÁNDEZ DE LA COMUNITAT VALENCIANA

( * ) Notice: Subject to any disclaimer, the term of this patent is extended or adjusted under 35 U.S.C. 154(b) by 0 days.

(21) Appl. No.: 17/624,392

(22) PCT Filed: Jul. 17, 2020

(86) PCT No.: PCT/ES2020/070464
§ 371 (c)(1),
(2) Date: Jan. 3, 2022

(87) PCT Pub. No.: WO2021/023901
PCT Pub. Date: Feb. 11, 2021

(65) Prior Publication Data
US 2022/0347472 A1   Nov. 3, 2022

(30) Foreign Application Priority Data
Aug. 2, 2019 (ES) .................................. 201930723

(51) Int. Cl.
*A61N 1/362* (2006.01)
*A61N 1/05* (2006.01)
*A61N 1/375* (2006.01)

(52) U.S. Cl.
CPC ........... *A61N 1/3625* (2013.01); *A61N 1/059* (2013.01); *A61N 1/3754* (2013.01)

(58) Field of Classification Search
None
See application file for complete search history.

(56) References Cited

U.S. PATENT DOCUMENTS 4,966,319 A * 10/1990 Fleming ................. A45C 11/00
  206/83
5,679,026 A * 10/1997 Fain ..................... A61N 1/3752
  439/651

(Continued)

FOREIGN PATENT DOCUMENTS

CN    108671400 A    10/2018
EP    0 599 567 A2   6/1994

(Continued)

OTHER PUBLICATIONS

International Search Report of PCT/ES2020/070464, dated Sep. 7, 2020.

*Primary Examiner* — Erica S Lee
(74) *Attorney, Agent, or Firm* — Collard & Roe, P.C.

(57) ABSTRACT

A fastening system for an electrical stimulation generator, with a generator and an electrode, has a casing for containing the generator that presents identical first and second openings, disposed on opposite sides; means for the connection of the electrode to the first or second opening in the casing formed by a first pass-through connector for the electrode, with a sealing element; an airtight closing element disposed at the opening of the casing opposite the one presenting the means for the connection of the electrode; a device for securing the electrode to the skin; and means for fastening the casing to the body of the patient.

12 Claims, 8 Drawing Sheets

(56) References Cited

U.S. PATENT DOCUMENTS

| | | | |
|---|---|---|---|
| 2011/0269350 A1* | 11/2011 | Mehdizadeh | A61N 1/3752 |
| | | | 439/638 |
| 2011/0313361 A1* | 12/2011 | Shipman | A61M 25/02 |
| | | | 604/180 |
| 2014/0172056 A1 | 6/2014 | Orinski | |
| 2014/0194678 A1 | 7/2014 | Wildhirt et al. | |
| 2015/0290455 A1* | 10/2015 | Bornzin | A61N 1/0551 |
| | | | 604/397 |
| 2016/0067502 A1* | 3/2016 | Bornzin | A61N 1/36017 |
| | | | 607/116 |
| 2018/0207427 A1* | 7/2018 | Webb | A61N 1/3756 |
| 2019/0160262 A1 | 5/2019 | Jones | |

FOREIGN PATENT DOCUMENTS

| | | |
|---|---|---|
| EP | 0 948 972 A2 | 10/1999 |
| WO | 2006/069548 A1 | 7/2006 |

\* cited by examiner

FASTENING SYSTEM FOR AN ELECTRICAL STIMULATION GENERATOR

CROSS REFERENCE TO RELATED APPLICATIONS

This application is the National Stage of PCT/ES2020/070464 filed on Jul. 17, 2020, which claims priority under 35 U.S.C. § 119 of Spanish Application No. P201930723 filed on Aug. 2, 2019, the disclosure of which is incorporated by reference. The international application under PCT article 21(2) was not published in English.

TECHNICAL FIELD OF THE INVENTION

The present invention corresponds to the technical field of the industry dedicated to the manufacture of medical devices, specifically in the field of cardiac stimulation.

BACKGROUND OF THE INVENTION

Cardiac stimulation systems consist of devices the function of which is to detect the electrical activity generated by the heart, and in the absence of said activity, to interpret it as an absence of a heartbeat and to provide an electric discharge which causes the heart contraction at a given power.

In detail, a cardiac stimulation system is made up of circuits and processors, housed together with the battery in a metal casing, usually made of titanium, and intended for performing the function of detecting electrical activity and generating pulses.

The system furthermore presents one, two, or three electrodes, depending on the type of cardiac stimulation required. These electrodes are connected in respective ports of the generator located in a silicone head and run from a central venous access of the patient to the desired heart chamber (right auricle or ventricle), being supported on or fixed to the endocardium. If the left ventricle is to be stimulated via the coronary sinus, the electrode is moved to the desired location.

The electrodes, formed by a metallic material covered with insulating element, receive electrical information from the heart and channel it to the processors in the casing. In the absence of electrical activity, there is emitted from the generator housed in the casing an electric discharge which is channeled to the endocardium (or epicardium in the electrodes of the coronary sinus), causing a heart contraction.

These cardiac stimulation systems may be permanent or temporary depending on the time the stimulation therapy will be maintained.

Current permanent systems are made up of increasingly smaller generators which reach a volume of 10 cm$^3$ and in which the generator is housed in the subcutaneous cellular tissue, usually in the anterior pectoral region of the patient. In this case, the electrodes are introduced through the subclavian or, in some cases, the internal jugular route to the superior vena cava and to the final location which can be the right auricle, the right ventricle, or the coronary venous network.

In temporary cardiac stimulation systems, the external generator which has typically been used and contains all the necessary elements (battery, processors, electrode connection ports) can reach a length of 15 cm and a weight of up to 1 kg.

Moreover, the electrodes used with these devices for temporary stimulation often lack a system for fixing to the endocardium, where said devices are supported solely on the inner heart surface.

These two features of the conventional temporary cardiac stimulation system mean that the patient must remain at absolute rest and with continuous monitoring in an Intensive Care Unit (ICU). The electrode-endocardium contact and the size of the generator mean that the system is unstable and prevents patient mobility.

The purpose of this temporary stimulation is to obtain time to complete the study on the patient which may conclude in spontaneous recovery or in the need for implanting a permanent pacemaker.

Materials of permanent stimulation systems are being used today for temporary cardiac stimulation as they provide greater safety. This technique consists of leaving the active fixing electrode externalized, connected to a permanent pacemaker generator. Use of these components provides an electrode-endocardium attachment with a safer and more stable active fixing that allows discharging the patient from the ICU so that their progress may continue in a hospitalization ward.

A fastening system for fastening this generator and the externalized electrode to the patient, providing the required safety, is not available today. In some cases, it is secured to the patient by means of dressings or sutured to the skin. This solution poses a series of problems given that the systems may come off easily and the generator may pull on the electrode, with the generator-electrode being disconnected, causing the stimulation to stop, or a cardiac rupture may even occur due to the direct pulling of the endocardium since the electrode is screwed thereon.

Likewise, the entire external system is exposed to the medium such that it can be colonized by bacteria and subsequently cause an infection in the patient.

The possibility of having an effective fastening system for all the externalized components, which increase the safety of these patients', preventing accidental detachments and possible infections as a result of contaminations due to the simple exposure of the system to the environment or to contact with healthcare personnel, would be desirable.

No external fastening device for temporary electrical cardiac stimulation systems of this type with permanent generators is known.

DESCRIPTION OF THE INVENTION

The fastening system for an electrical stimulation generator herein proposed comprises a generator for cardiac stimulation, such as a pacemaker, a defibrillator, a resynchronizer; a neurostimulation mechanism or another similar generator disposed externally with respect to the body of the patient, as well as an electrode that presents a first end for connection to the heart of the patient and a second end for connection to said generator.

This system comprises a casing for containing the generator therein. This casing has identical first and second openings disposed on opposite sides thereof.

Likewise, the system comprises means for the connection of the electrode to the first or second opening of the casing formed by a first pass-through connector for the second end of the electrode. Said first connector has a sealing element therein.

Furthermore, the system has an airtight closing element which is disposed at the opening of the casing opposite the one presenting the means for the connection of the electrode.

The system in turn comprises a device for securing the electrode to the skin with means for anchoring to said electrode and means for adhering to the torso of the patient. It furthermore presents means for fastening the casing to the body of the patient.

A significant improvement with respect to the state of the art is achieved with the fastening system for an electrical stimulation generator herein proposed.

In other words, a fastening system with a highly relevant improvement in terms of safety against possible detachments is thereby achieved, which leads to a reduction in terms of possible accidental disconnections of the electrode from the generator or even of possible cardiac ruptures caused by the electrode being pulled during connection thereof to the endocardium.

Moreover, the airtightness achieved in all the components of the system allows infections related to intravascular systems to be significantly reduced, thereby eliminating any possible path for bacteria to enter the blood.

Likewise, the present invention is a system which can be secured both on the right side and on the left side of the body, as a result of the two openings of the casing which are disposed on both sides thereof and between which the airtight closing element and the first connector can be interchanged, allowing the electrode to come out from the two directions.

It is therefore a system that allows solving the drawbacks existing today in temporary electrical cardiac stimulation systems with permanent external generators in a simple and effective manner.

BRIEF DESCRIPTION OF THE DRAWINGS

For the purpose of helping to better understand the features of the invention according to a preferred practical embodiment thereof, a series of drawings is provided as an integral part of said description in which the following is depicted in an illustrative and non-limiting manner:

FIGS. 6.1 and 6.2 show perspective and sectional views, respectively, of the second connector for the means for anchoring the electrode of a fastening system for an electrical stimulation generator for a preferred embodiment of the invention.

DETAILED DESCRIPTION OF A PREFERRED EMBODIMENT OF THE INVENTION

In view of the mentioned figures, it can be observed how in a preferred embodiment of the invention the fastening system (1) for an electrical stimulation generator (2) comprises a generator (2) for cardiac stimulation, such as a pacemaker, a defibrillator, a resynchronizer, a neurostimulation mechanism or another similar generator disposed externally with respect to the body of the patient (3) and an electrode (5) that presents a first end (5.1) for connection to the heart of the patient (3) and a second end (5.2) for connection to said generator (2).

This device comprises a casing (4) for containing said generator (2) therein, means for the connection of the electrode (5), an airtight closing element (10), a device (6) for securing the electrode (5) to the skin, and means for fastening the casing (4) to the body of the patient (3).

Figure 1:
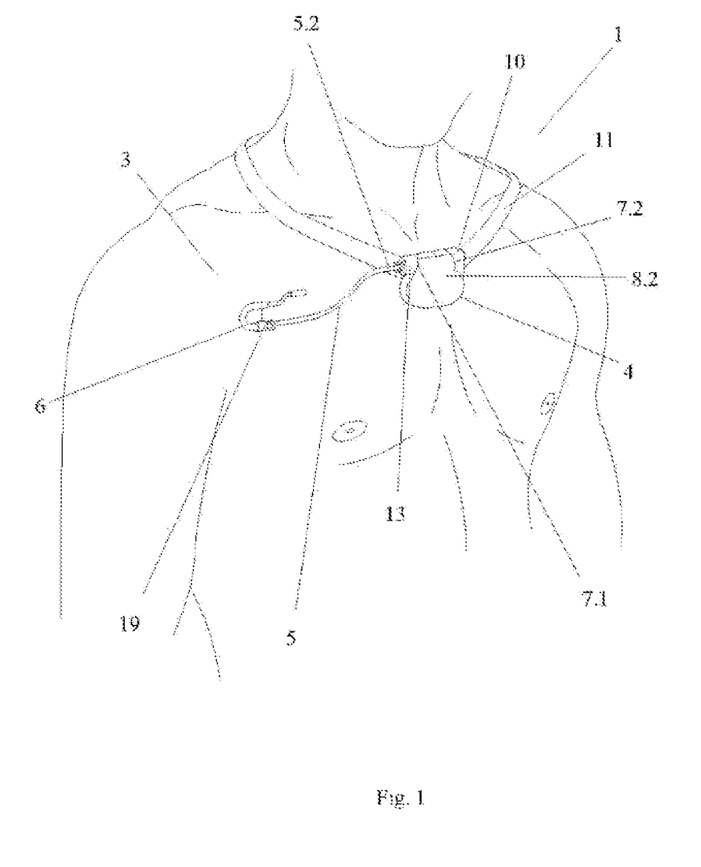
FIG. 1 shows a perspective view of a fastening system for an electrical stimulation generator with the casing closed and secured to the neck of a patient for a preferred embodiment of the invention.
Figure 2:
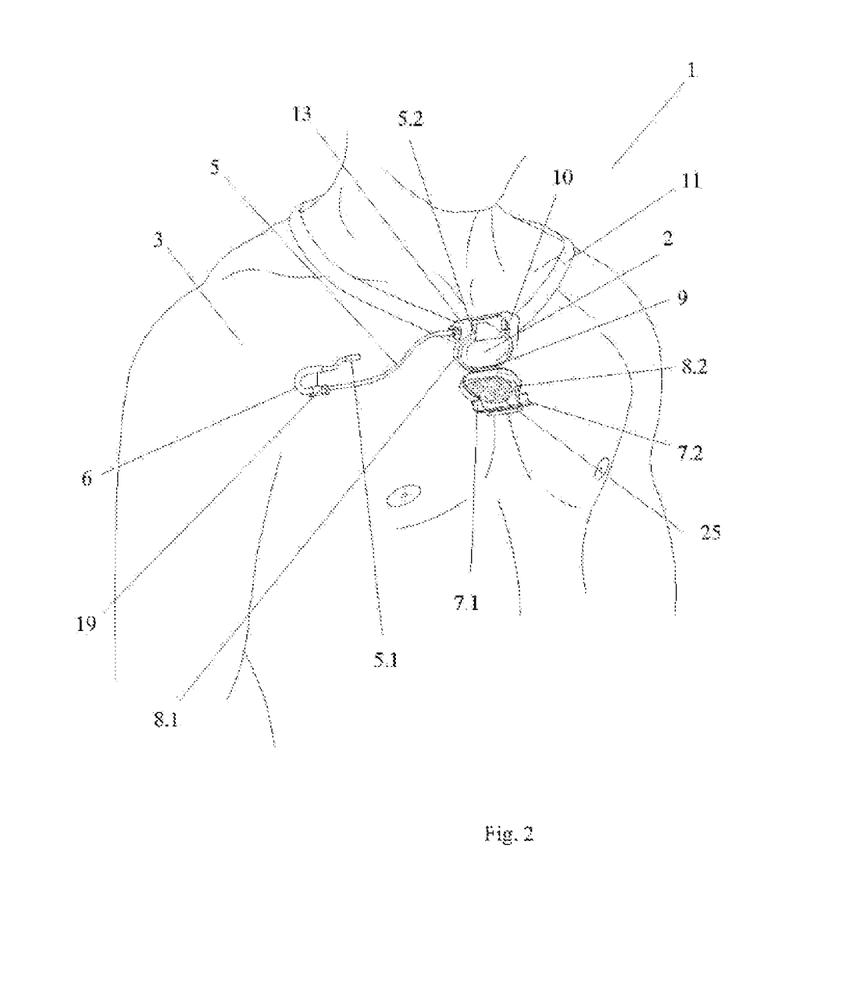
FIG. 2 shows a perspective view of a fastening system for an electrical stimulation generator with the casing open and secured to the neck a patient for a preferred embodiment of the invention.
Figure 3:
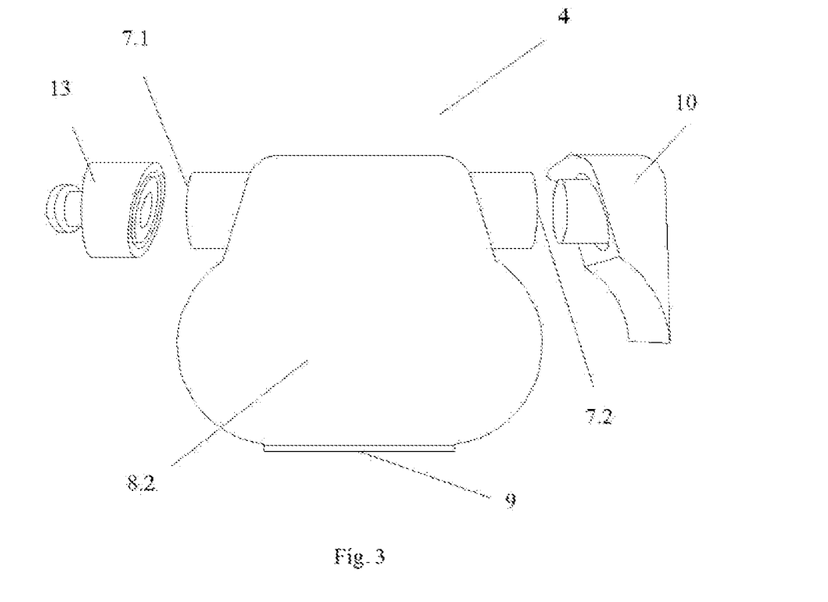
FIG. 3 shows a view of the casing of a fastening system for an electrical stimulation generator with the connector for the electrode and the airtight closing element for a preferred embodiment of the invention.

As shown in FIGS. 1 to 3, the casing (4) presents identical first and second openings (7.1, 7.2) disposed on opposite sides thereof.

In this preferred embodiment of the invention, as can be seen in FIG. 2, the casing (4) is formed by a rear part (8.1) in contact with the body of the patient (3) and a front part (8.2), joined together by hinged means (9), and comprises closing means at an end opposite the hinged means (9). In this embodiment, these closing means consist of the fitting of the first connector (13) in the first opening (7.1) of the casing (4) and the fitting of the closing element (10) in the second opening (7.2) thereof. Said fitting of both allows keeping both the rear part and the front part (8.1, 8.2) of the casing (4) joined to one another.

In turn, as shown in FIGS. 1 and 2, in this embodiment, the means for fastening the casing (4) to the body of the patient (3) are formed by a longitudinal and flexible strap (11) suitable for placement thereof around the neck of the patient (3) like a necklace.

Figure 4:
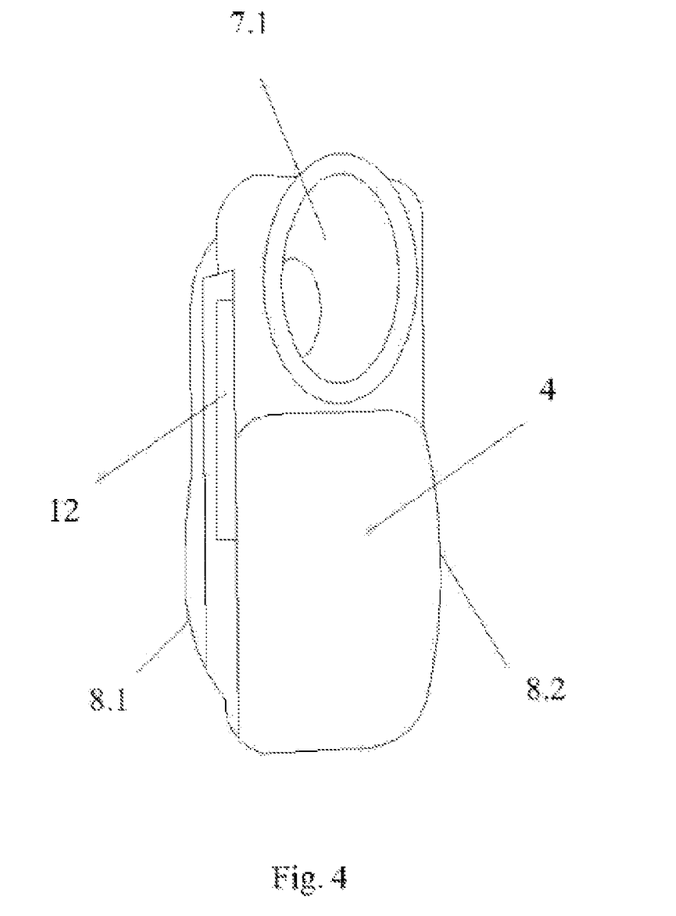
FIG. 4 shows a side view of the casing of a fastening system for an electrical stimulation generator for a preferred embodiment of the invention.

Therefore, as shown in FIG. 4, the casing (4) comprises on the external surface of the rear part (8.1) an eyelet (12) suitable for holding the longitudinal strap (11) therein. The strap (11) is therefore passed through the eyelet (12) of the casing (4) and is firmly secured to the neck of the patient (3).

In this system (1), the means for the connection of the electrode (5) are formed by a first pass-through connector (13) for the second end (5.2) of the electrode (5), having a sealing element (14) therein.

In this preferred embodiment of the invention, the electrode (5) is connected to the generator (2) through the first opening (7.1), so the first connector (13) is disposed in said first opening (7.1), but in the case in which the connection is to be made on the other side of the patient's body, the electrode (5) would be connected through the second opening (7.2).

In this preferred embodiment of the invention, the electrode (5) comprises a sheath for covering same, in the externalized part thereof, between the point where it comes out through the first opening (7.1) of the casing (4), in this case, until the second connector (19) for anchoring to the device (6) for securing to the skin. In this case, the sheath is furthermore preferably formed by a plastic material having retractable properties.

Figure 8:
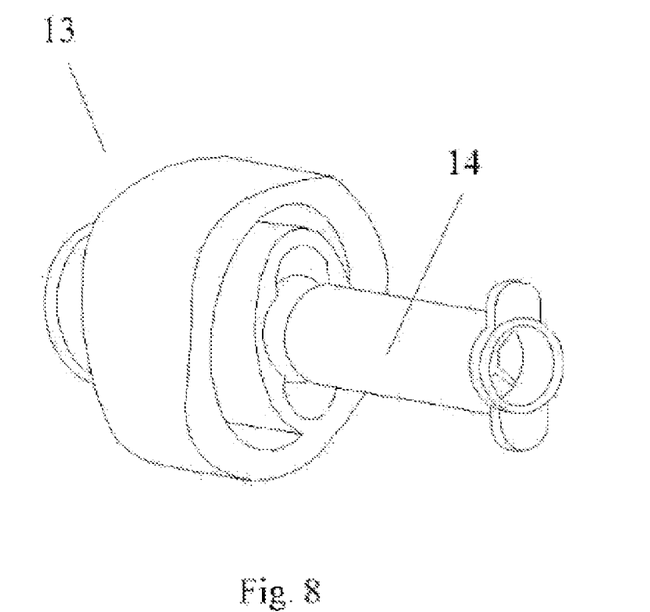
FIG. 8 shows an exploded view of the first connector and the sealing element of a fastening system for an electrical stimulation generator for a preferred embodiment of the invention.
Figure 9:
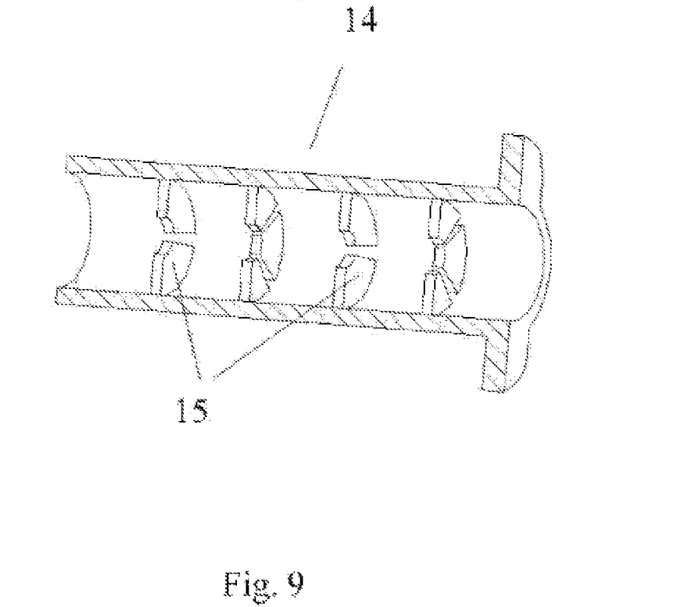
FIG. 9 shows a sectioned view of the sealing element of the first connector of a fastening system for an electrical stimulation generator for a preferred embodiment of the invention.

As shown in FIGS. 8 and 9, the sealing element (14) of the first connector (13) comprises internal disks (15) allowing the passage of the electrode (5) while at the same time providing airtightness to said first opening (7.1) in this case.

Given that the electrode (5) is connected to the generator (2) through the first opening (7.1), it is the second opening (7.2) of the casing (4) which presents an airtight closing element (10).

Moreover, the device (6) for securing the electrode (5) to the skin presents means for anchoring to said electrode (5) and means for adhering to the torso of the patient (3).

In this preferred embodiment of the invention, as shown in FIGS. 1, 2, 5, and 7, the device (6) for securing to the skin has a tubular shape with first and second ends (6.1, 6.2) and at least one semicircular segment (16) between them. In this specific embodiment, this device (6) for securing to the skin comprises two additional straight segments (17) between the semicircular segment (16) and the first and second ends (6.1, 6.2), respectively, of said device (6) for securing to the skin, as can be seen in said figures.

Figure 5:
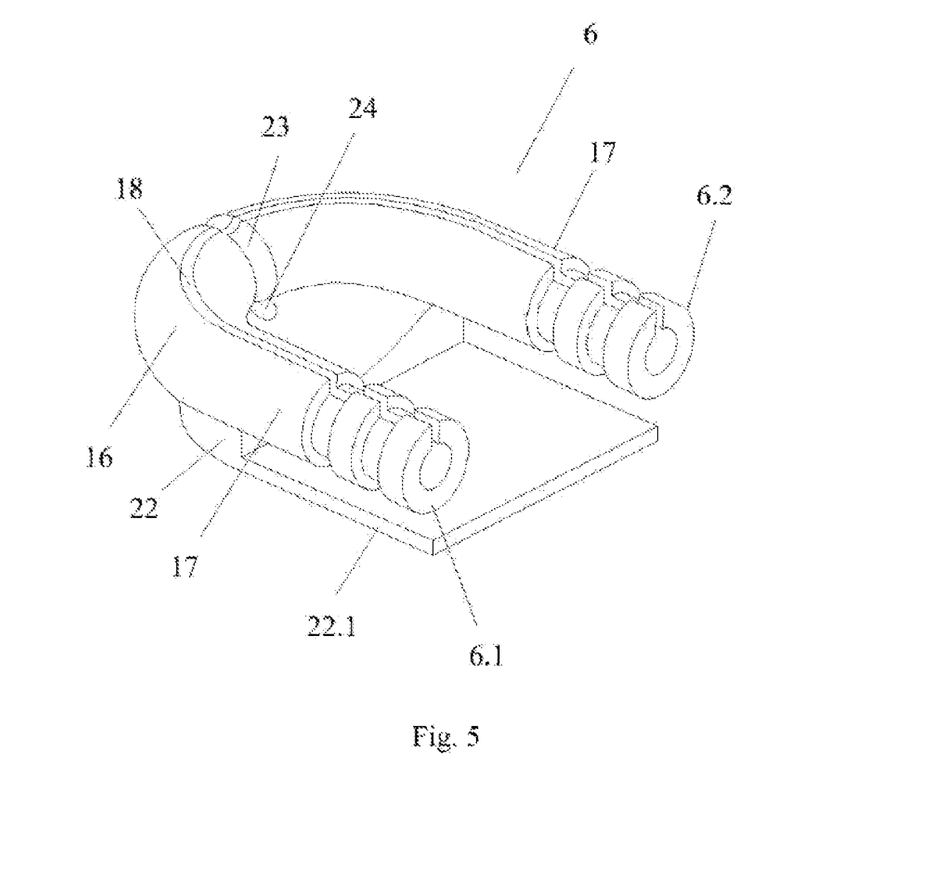
FIG. 5 shows a perspective view of the device for securing the electrode to the skin of a fastening system for an electrical stimulation generator for a preferred embodiment of the invention.
Figure 7:
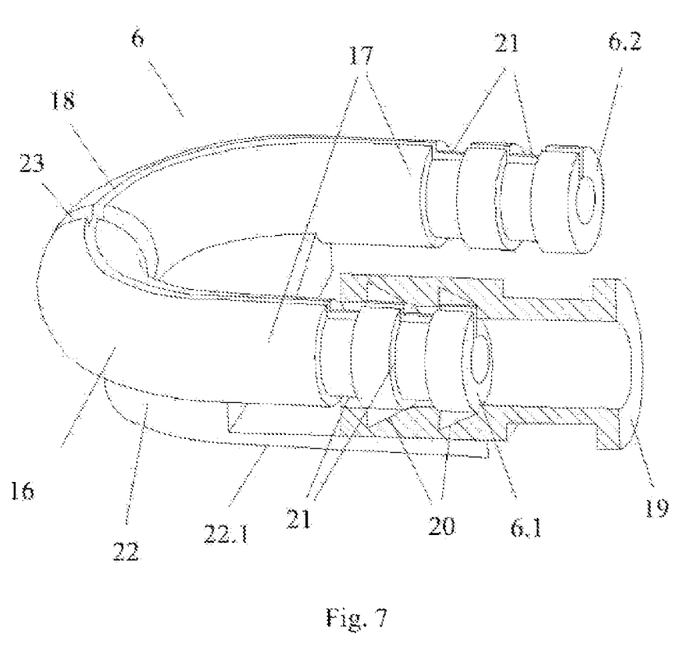
FIG. 7 shows a perspective view of the device for securing the electrode to the skin and the second connector at an end thereof, of a fastening system for an electrical stimulation generator for a preferred embodiment of the invention.

FIGS. 5 and 7 show that the device (6) for securing to the skin comprises a groove (18) communicating the inside of the device (6) for securing to the skin with the outside along the entire length thereof between both first and second ends (6.1, 6.2). The dimensions of said groove (18) are such that they allow the introduction of the electrode (5) inside the entire tubular path of the device (6) for securing to the skin from the first end (6.1) to the second end (6.2) thereof.

Figure 61:
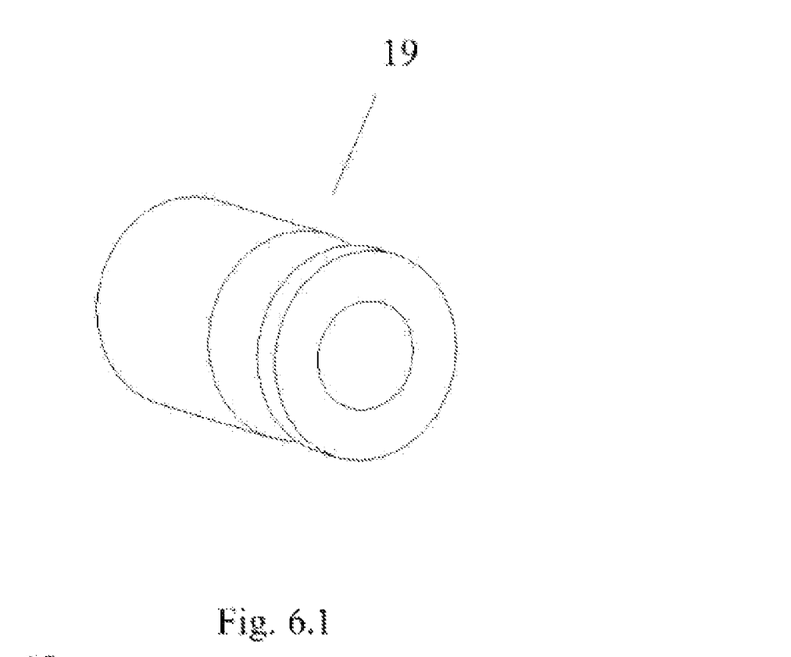
Figure 62:
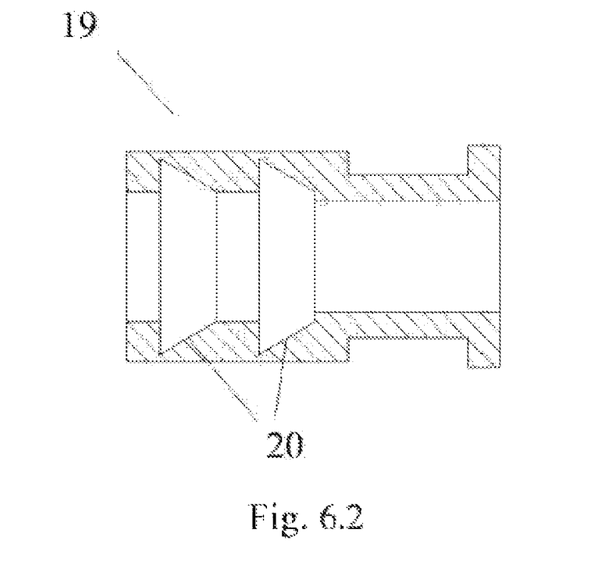

In this preferred embodiment of the invention, the means for anchoring the electrode (5) to the device (6) for securing to the skin are formed by a second connector (19), shown in FIGS. 6.1, 6.2, and 7, suitable for connection thereof in the first or second end (6.1, 6.2) of said device (6) for securing to the skin, in this case the first end (6.1) thereof.

This second connector (19) presents first notches (20) on its inner surface, whereas the first and second ends (6.1, 6.2) of the device (6) for securing to the skin present on their outer surface second notches (21) suitable for fitting with the first notches (20) of said second connector (19).

In this preferred embodiment of the invention, the means for adhering the device (6) for securing to the skin are formed by a protruding element (22) which protrudes from the semicircular segment (16) of said device (6) for securing to the skin, with a face (22.1) opposite said semicircular segment (16) and with an adhesive thereon.

Likewise, this device (6) for securing to the skin comprises means for tying the electrode (5) thereto, so as to fix the electrode (5) even more firmly to said device. These means for tying are formed by a silk thread or the like (not depicted in the figures), a third notch (23) around the contour of the central section of the semicircular segment (16), and a through hole (24) disposed between said notch and the protruding element (22) of the means for adhering such that it coincides with said third notch (23). This third notch (23) is suitable for the fitting of said silk thread and for tying same around the electrode (5).

A silk thread can therefore be passed through the through hole (24) and is fitted in the third notch (23) so that, when it is tied, the thread constricts the electrode (5), fixing it in place inside the groove (18) of the device (6) for securing to the skin.

In this preferred embodiment of the invention, the system (1) further comprises a padded element (25) on the inner surface of both front and rear parts (8.1, 8.2) to thereby dampen the contact of the generator (2) with said front and rear parts (8.1, 8.2) of the casing (4).

The described embodiment constitutes a mere example of the present invention, therefore, the specific details, terms, and phrases used in the present specification must not be considered limiting but understood solely as a basis for the claims and as a representative basis which provides a comprehensible description, as well as sufficient information, to one skilled in the art to apply the present invention.

The invention claimed is:

1. A fastening system (1) for an electrical stimulation generator (2), comprising:
    a generator (2) for cardiac stimulation disposed externally with respect to a body of a patient (3),
    an electrode (5) that presents a first end (5.1) configured for connection to a heart of the patient (3) and a second end (5.2) configured for connection to said generator (2),
    a casing (4) configured for containing the generator (2) therein, the casing having identical first and second openings (7.1, 7.2) disposed on opposite sides thereof;
    means for the connection of the electrode (5) to one of the first or second opening (7.1, 7.2) in the casing (4) and being formed by a first pass-through connector (13) for the second end (5.2) of the electrode (5), wherein the first pass-through connector (13) has a sealing element (14) therein;
    an airtight closing element (10) disposed at the other of the first or second opening in the casing (4) opposite the one of the first or second opening presenting the means for the connection of the electrode (5);
    a device (6) configured for securing the electrode (5) to the skin having means configured for anchoring to said electrode (5) and means configured for adhering to the torso of the patient (3); and
    means configured for fastening the casing (4) to the body of the patient (3),
    wherein the device (6) configured for securing to the skin has a tubular shape with first and second ends (6.1, 6.2) and at least one semicircular segment (16) between them, wherein the device (6) for securing to the skin comprises a groove (18) communicating an inside of the device (6) configured for securing to the skin with an outside along an entire length thereof between both first and second ends (6.1, 6.2), the groove (18) having dimensions that allow the fitting of the electrode (5) inside the device (6) for securing to the skin from the first end (6.1) to the second end (6.2) thereof, and
    further comprising means for anchoring the electrode (5) to the device (6) configured for securing to the skin formed by a second connector (19) suitable for connection thereof at the first or second end (6.1, 6.2) of said device (6) configured for securing to the skin, wherein the second connector (19) presents first notches (20) on an inner surface, and the first and second ends (6.1, 6.2) of said device (6) configured for securing to the skin present on their outer surface second notches (21) suitable for fitting with the first notches (20) of the second connector (19).

2. The system (1) according to claim 1, further comprising means for adhering formed by a protruding element (22) which protrudes from the semicircular segment (16) of the device (6) configured for securing to the skin, with a face (22.1) opposite said semicircular segment (16) and with an adhesive thereon.

3. The system according to claim 2, wherein the device (6) configured for securing to the skin comprises means for tying the electrode (5) thereto.

4. The system according to claim 1, wherein the device (6) configured for securing to the skin comprises two additional straight segments (17) between the semicircular segment (16) and the first and second ends (6.1, 6.2), respectively, of said device (6) for securing to the skin.

5. The system according to claim 1, wherein the sealing element (14) of the first pass-through connector (13) comprises internal disks (15) allowing the passage of the electrode (5).

6. The system according to claim 1, wherein the casing (4) is formed by a rear part (8.1) in contact with the body of the patient (3) and a front part (8.2), joined together by hinged means (9) and wherein fitting of the first pass-through connector (13) in one of said first or second openings and fitting of the closing element (10) in the other of the first or second openings (7.1, 7.2) of the casing (4) forms closing means at an end opposite the hinged means (9).

7. The system according to claim 6, wherein the means configured for fastening the casing (4) to the body of the patient (3) are formed by a longitudinal and flexible strap (11) configured for placement thereof around a neck of the patient (3).

8. The system according to claim 7, wherein the casing (4) comprises an eyelet (12) on the external surface of the rear part (8.1), the eyelet (12) being configured for holding the longitudinal and flexible strap (11) therein.

9. The system according to claim 1, further comprising a sheath covering the electrode between the first pass-through connector (13) and the second connector (19).

10. The system according to claim 9, wherein the sheath is formed by a plastic material and has retractable properties.

11. The system according to claim 1, wherein the casing (4) has a front part and a rear part and further comprising a padded element (25) on an inner surface of both front and rear parts (8.1, 8.2) of the casing (4).

12. A fastening system (1) for an electrical stimulation generator (2), comprising:
- a generator (2) for cardiac stimulation disposed externally with respect to a body of a patient (3),
- an electrode (5) that presents a first end (5.1) configured for connection to a heart of the patient (3) and a second end (5.2) configured for connection to said generator (2),
- a casing (4) configured for containing the generator (2) therein, the casing having identical first and second openings (7.1, 7.2) disposed on opposite sides thereof;
- means for the connection of the electrode (5) to one of the first or second opening (7.1, 7.2) in the casing (4) and being formed by a first pass-through connector (13) for the second end (5.2) of the electrode (5), wherein the first pass-through connector (13) has a sealing element (14) therein;
- an airtight closing element (10) disposed at the other of the first or second opening in the casing (4) opposite the one of the first or second opening presenting the means for the connection of the electrode (5);
- a device (6) configured for securing the electrode (5) to the skin having means configured for anchoring to said electrode (5) and means configured for adhering to the torso of the patient (3); and
- means configured for fastening the casing (4) to the body of the patient (3), wherein the device (6) configured for securing to the skin has a tubular shape with first and second ends (6.1, 6.2) and at least one semicircular segment (16) between them, wherein the device (6) for securing to the skin comprises a groove (18) communicating an inside of the device (6) configured for securing to the skin with an outside along an entire length thereof between both first and second ends (6.1, 6.2), the groove (18) having dimensions that allow the fitting of the electrode (5) inside the device (6) for securing to the skin from the first end (6.1) to the second end (6.2) thereof, further comprising means for adhering formed by a protruding element (22) which protrudes from the semicircular segment (16) of the device (6) configured for securing to the skin, with a face (22.1) opposite said semicircular segment (16) and with an adhesive thereon, wherein the device (6) configured for securing to the skin comprises means for tying the electrode (5) thereto, and wherein the means for tying the electrode (5) are formed by a silk thread, a third notch (23) around the contour of a central section of the semicircular segment (16), and a through hole (24) disposed between the third notch and the protruding element (22) of the means for adhering such that it coincides with said third notch (23), and wherein the third notch (23) is suitable for the fitting of said silk thread and for tying same around the electrode (5).

* * * * *